US011786512B2

(12) United States Patent
Chinnari et al.

(10) Patent No.: US 11,786,512 B2
(45) Date of Patent: Oct. 17, 2023

(54) STABLE PHARMACEUTICAL COMPOSITIONS OF DIHYDROERGOTAMINE MESYLATE

(71) Applicant: Slayback Pharma LLC, Princeton, NJ (US)

(72) Inventors: Harish Govindaraja Setty Chinnari, Hyderabad (IN); Somashekhar Battini, Hyderabad (IN); Jagdish Lotan Lohar, Pune (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 444 days.

(21) Appl. No.: 17/028,863

(22) Filed: Sep. 22, 2020

(65) Prior Publication Data
US 2021/0085657 A1 Mar. 25, 2021

(30) Foreign Application Priority Data
Sep. 23, 2019 (IN) .............................. 201941038367

(51) Int. Cl.
*A61K 9/00* (2006.01)
*A61K 47/02* (2006.01)
*A61K 47/20* (2006.01)
*A61K 47/10* (2017.01)
*A61K 31/4985* (2006.01)
*A61K 31/437* (2006.01)

(52) U.S. Cl.
CPC .......... *A61K 31/437* (2013.01); *A61K 9/0019* (2013.01); *A61K 31/4985* (2013.01); *A61K 47/02* (2013.01); *A61K 47/10* (2013.01); *A61K 47/20* (2013.01)

(58) Field of Classification Search
CPC .. A61K 31/4985; A61K 9/0019; A61K 47/10; A61K 47/20
See application file for complete search history.

(56) References Cited

U.S. PATENT DOCUMENTS

| 4,138,565 | A | 2/1979 | Ehrhardt et al. |
| 5,942,251 | A | 8/1999 | Merkus |
| 6,495,535 | B1 | 12/2002 | Plachetka et al. |
| 6,770,262 | B2 | 8/2004 | Lehman et al. |
| 7,994,197 | B2 | 8/2011 | Cook et al. |
| 8,148,377 | B2 | 4/2012 | Cook et al. |
| 9,394,314 | B2 | 7/2016 | Kellerman et al. |
| 2019/0000753 | A1* | 1/2019 | Narasimha Murthy ..................... A61K 47/12 |

OTHER PUBLICATIONS

Shafqat et al; Updated Evaluation of IV Dihydroergotamine (DHE) for Refractory Migraine: Patient Selection and Special Considerations; Journal of Pain Research 2020:13 859-864.
D.H.E. 45® (dihydroergotamine mesylate) Injection, USP, publication date: Aug. 2008, available Online Sep. 1, 2009. Retrieved from the Internet on Sep. 16, 2020 from <URL: https://www.accessdata.fda.gov/drugsatfda_docs/label/2009/005929s044lbl.pdf>.

\* cited by examiner

*Primary Examiner* — Timothy P Thomas
(74) *Attorney, Agent, or Firm* — Birch, Stewart, Kolasch & Birch, LLP

(57) ABSTRACT

The present invention relates to stable pharmaceutical compositions of dihydroergotamine mesylate or other pharmaceutically acceptable salts thereof and methods for preparing the compositions particularly for the treatment of migraine headaches. The invention further relates to stable injectable composition comprising dihydroergotamine or its pharmaceutically acceptable salts thereof, wherein the composition has a pH from about 5.0 to about 6.0. Further, the present invention relates to a method of treating migraine comprising providing a stable pharmaceutical composition for parenteral administration comprising dihydroergotamine mesylate, wherein the pH of the composition ranges from 5.0 to 6.0 and, wherein the composition comprises no greater than 3% of total impurities as determined by HPLC.

11 Claims, No Drawings

STABLE PHARMACEUTICAL COMPOSITIONS OF DIHYDROERGOTAMINE MESYLATE

CROSS-REFERENCE TO RELATED APPLICATIONS

This application claims foreign priority to Indian Application No. IN, 201941038367 filed on Sep. 23, 2019, which is incorporated herein by reference in its entirety.

FIELD OF THE INVENTION

The present invention relates to stable pharmaceutical compositions of dihydroergotamine (DHE) or its pharmaceutically acceptable salts thereof and methods for preparing the compositions particularly for the treatment of migraine headaches. The invention further relates to stable injectable compositions comprising dihydroergotamine or its pharmaceutically acceptable salts thereof, wherein the composition has a pH ranging from about 5.0 to about 6.0.

BACKGROUND OF THE INVENTION

Dihydroergotamine (DHE) is an ergot alkaloid derivative of substances produced by rye fungus. DHE is a drug used in migraine therapy since a long time; especially useful for patients with migraine attacks not responsive to triptans, who have greater burden from migraine, and in refractory migraine.

DHE can be delivered via several routes including intravenous (IV), intramuscular (IM), subcutaneous (SC), intranasal (IN), oral, and orally inhaled. Oral DHE was first formulated in 1943. It was not until much later that the IV formulation and the IM formulation of DHE were studied formally and shown to be effective in the treatment of migraine. DHE has very low rectal, oral, sublingual and intranasal bioavailability (only 2% to 10% of the administered dose reaches the systemic circulation). Hence, these administration routes result in relatively slow onset of therapeutic efficacy, ranging from 45 minutes for intranasal to 2 hours for oral or sublingual delivery. In comparison, parenteral administration of dihydroergotamine has higher bioavailability and rapid onset of action, usually much less than 30 minutes.

DHE is currently marketed as an injection and a nasal spray under the brand names D.H.E. 45® (DHE 45) and Migranal® respectively. DHE 45 is a composition comprising 1 mg/mL of Dihydroergotamine mesylate (DHE mesylate). DHE 45 is a clear, colorless solution supplied in sterile ampules for intravenous, intramuscular or subcutaneous administration as 1 mg/ml solution. DHE 45 contains alcohol, 6.1% by volume; glycerin, 15% by weight; and water for injection. In addition, methane sulfonic acid and/or sodium hydroxide are used for pH adjustment in the range of 3.4-4.9.

DHE 45 suffers a number of deficiencies with respect to the quality and purity due to which neither the potency nor the safety of the drug product may be adequately assured. There exists a need for improved pharmaceutical compositions of DHE mesylate with minimal levels of degradants, while guaranteeing sterility. There is a need for an improved composition of DHE mesylate that is stable, and undergoes minimal to zero degradation.

The applicants found that the inventive compositions of DHE mesylate prepared according to the present invention have a better stability profile when compared to DHE 45. Furthermore, the applicants found that the rate of epimerization of DHE mesylate is higher at a lower pH of less than 4.0, while it is significantly lesser towards pH of more than 5.0. Maintaining the pH above 5.0 in the compositions prepared according to the present invention results in a better stability profile when compared to DHE 45 maintained at a pH of 3.4-4.9.

It would be desirable for DHE mesylate compositions to remain stable over relevant period of time under suitable storage conditions and to be suitable for administration by intravenous or other parenteral routes. The present invention fulfils this need by developing improved DHE compositions and providing methods for safer use and improved standard of patient care.

SUMMARY

A stable pharmaceutical composition for parenteral administration comprising dihydroergotamine mesylate; wherein pH of the composition ranges from 5.0 to 6.0 and; wherein the composition comprises no greater than 3% of total impurities as determined by HPLC.

A method of treating migraine in a patient in need thereof, the method comprising providing a stable pharmaceutical composition for parenteral administration comprising dihydroergotamine mesylate; wherein the pH of the composition ranges from 5.0 to 6.0 and; wherein the composition comprises no greater than 3% of total impurities as determined by HPLC.

The composition as described above, further comprising alcohol, glycerine and an optional pH adjusting agent; wherein the pH adjusting agent is methane sulfonic acid, sodium hydroxide or a combination of both; and wherein the pH of the composition is from about 5.2 to about 5.5.

A method of preparing the composition as described above comprising: (i) dispensing water for injection under nitrogen purging; (ii) adding alcohol, followed by glycerine, to water for injection to form a clear solution; (iii) adding dihydroergotamine mesylate to the clear solution; (iv) optionally adjusting the pH with methane sulfonic acid or with sodium hydroxide to 5.0-6.0; and (v) adding sufficient quantity of water for injection to make up the final volume.

The composition as described above, wherein the dihydroergotamine mesylate concentration ranges from about 0.1 mg/mL to about 1.5 mg/mL, preferably from about 0.5 mg/mL to about 1.0 mg/m L.

The composition as described above, wherein the dihydroergotamine mesylate concentration is about 1 mg/mL and; wherein the composition has a pH from about 5.2 to about 5.5.

The composition as described above, comprising no greater than 3% of total impurities as determined by HPLC.

The composition as described above, comprising no greater than 2% of total impurities as determined by HPLC.

The composition as described above, comprising no greater than about 2% of 2'-epi-9,10-dihydro ergotamine (6aR,9R,10aR)—N-[(2R,5S,10 aS,10bS)-5-benzyl-10b-hydroxy-2-methyl-3,6-dioxooctahydro-8H-oxazolo[3,2-a]pyrrolo[2, e]pyrazin-2-yl]-7-methyl-4,6,6a,7,8,9,10,10a-octahydroindolo[4,3-fg]quinoline-9-carboxamide.

The composition as described above, comprising no greater than 1% of 2'-epi-9,10-dihydro ergotamine(6aR,9R, 10aR)—N-[(2R,5S,10aS,10bS)-5-benzyl-10b-hydroxy-2-methyl-3,6-dioxooctahydro-8H-oxazolo[3,2-a]pyrrolo[2, e]pyrazin-2-yl]-7-methyl-4,6,6a,7,8,9,10,10a-octahydroindolo[4,3-fg]quinoline-9-carboxamide.

The composition as described above, comprising no greater than 0.5% of 2'-epi-9,10-dihydro ergotamine(6aR,9R,10aR)—N-[(2R,5S,10aS,10bS)-5-benzyl-10b-hydroxy-2-methyl-3,6-dioxooctahydro-8H-oxazolo[3,2-a]pyrrolo[2,e]pyrazin-2-yl]-7-methyl-4,6,6a,7,8,9,10,10a-octahydroindolo[4,3-fg]quinoline-9-carboxamide.

The composition as described above, wherein said composition is stable for at least 3 months at 25° C. and 60% relative humidity.

The composition as described above, wherein said composition is stable for at least 24 months when stored under room temperature.

DETAILED DESCRIPTION

The invention is defined with reference to the appended claims. With respect to the claims, the glossary that follows provides the relevant definitions. Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

The terms "about" and "approximate", when used along with a numerical variable, generally means the value of the variable and all the values of the variable within an experimental error (e.g. 95% confidence interval for the mean) or within a specified value±10% or within a broader range.

As used herein, "a," "an," "the," "at least one," and "one or more" are used interchangeably. As used herein, the term "or" is generally employed in its usual sense including "and/or" unless the content clearly dictates otherwise.

The term "dihydroergotamine" as used herein refers to dihydroergotamine or a pharmaceutically acceptable salt(s) such as dihydroergotamine mesylate, dihydroergotamine tartrate and the like.

The term "migraine" as used herein refers to migraine with or without aura. The term "human subject" as used herein refers to a human who may be suffering from migraine or cluster headache.

The term "treatment" as used herein includes any treatment of a condition or disease in a subject, or particularly a human, and may include: (i) preventing the disease or condition from occurring in the subject which may be predisposed to the disease but has not yet been diagnosed as having it; (ii) inhibiting the disease or condition i.e., arresting its development; relieving the disease or condition—causing regression of the condition; or (iii) ameliorating or relieving the conditions caused by the disease, i.e., symptoms of the disease. "Treatment," as used herein, could be used in combination with other standard therapies or alone.

The term "effective amount" refers to that amount which is sufficient to effect treatment, as defined herein, when administered to a subject in need of such treatment. The effective amount will vary depending on the subject and disease state being treated, the severity of the affliction and the manner of administration, and may be determined routinely by one of ordinary skill in the art.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

A "dosage", "dosage form", "dose unit" or "dose" as used herein means the amount of a pharmaceutical formulation comprising therapeutically active agent(s) administered at a time. "Dosage", "dosage form", "dose unit" or "dose" includes administration of one or more units of pharmaceutical formulation administered at the same time.

The terms "composition" and "formulation" refer to a pharmaceutical composition administered to a patient in need of treatment, which is typically in the form of a lyophilized powder, powder, solution, suspension, emulsion and like.

The term "stable" refers to both the physical and chemical stability of a composition in any form, such as a solution. A composition is said to be stable if it exhibits minimal change over time relative to when it is manufactured. Stability is measured at various time points through a planned product expiration date with evaluation criteria including such items as appearance, levels of particulate matter, pH, content of active ingredient(s), and levels of degradation products, impurities, or related substances.

The term "shelf life" means the period beginning from manufacture of a formulation beyond which the formulation cannot be expected beyond reasonable doubt to yield the therapeutic outcome approved by a government regulatory agency.

The term "total impurities" means the sum of all impurities including, but not limited to impurity A, impurity B, impurity C, impurity D, impurity E and impurity I—as individually defined in table 3—that are present in the inventive composition. The determination of the presence of impurities is made by HPLC at a wavelength of 220 nm after at least about one year at a temperature of from about 5° C. to about 25° C.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

The pharmaceutical compositions described herein may be provided in any form suitable for injection. To prepare such compositions, active drug(s) are dissolved or suspended in a parenterally acceptable liquid vehicle. In certain non-limiting embodiments, dihydroergotamine composition is formulated as a liquid and provided in the form of a solution, suspension, or emulsion. The pharmaceutically acceptable liquid vehicle or solvent may comprise water for injection, saline, alcohol, ethanol, glycerine, polyol (for example, propylene glycol, and polyethylene glycol, and the like), dimethylacetamide, N-methylpyrrolidone, dimethyl sulfoxide, ringer's solution, isotonic sodium chloride solution, or suitable mixtures thereof.

The compositions of the present invention may be administered in any conventional manner. It will be readily appreciated by those skilled in the art how to administer compositions of the present invention to a human or an animal. The composition is preferably suitable for parenteral administration, including, but not limited to intravenous, subcutaneous, intramuscular and intraperitoneal administration.

In certain non-limiting embodiments, dihydroergotamine is formulated as a composition, wherein dihydroergotamine is the only therapeutically active ingredient present in the composition. In another non-limiting embodiment, dihydroergotamine is formulated as a composition, wherein the dihydroergotamine is formulated in combination with at least one or more other therapeutically active ingredient.

According to present invention, the stable composition of the present invention is in a form selected from solution, suspension, or emulsion suitable for parenteral administration comprising dihydroergotamine or a pharmaceutically acceptable salt thereof with one or more parenterally acceptable excipients.

In another aspect of the above embodiments, the pharmaceutical dosage form of dihydroergotamine of the present application optionally comprises one or more pharmaceutically acceptable excipients that are generally known in the art for injectable composition. Such excipients include, but are not limited to solvents, solubilizers, preservatives, antioxidants, buffers, tonicity modifying agents, pH adjusting agents and like or combinations thereof.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent.

In certain embodiments, the pharmaceutical compositions prepared according to the invention may optionally contain pharmaceutically acceptable excipients, including antioxidants, buffers, tonicity modifying agents, preservatives, stabilizing agents, solubilizers, or pH adjusting agents.

In some embodiments, a pharmaceutical composition of the invention can be formulated for long-term storage of dihydroergotamine at room temperature in presence of a suitable pharmaceutically-acceptable excipient. The pharmaceutically-acceptable excipients can increase the half-life of dihydroergotamine when stored at any temperature, such as room temperature. The presence of the pharmaceutical excipients can decrease the rate of decomposition of dihydroergotamine at any temperature, such as room temperature.

The pharmaceutical compositions may optionally contain an anti-oxidant or a stabilizing agent in a stabilizing amount. Examples of antioxidant and stabilizing agents may also include by way of example and without limitation, methionine, glycerol, monothioglycerol, propylene glycol, phenol, EDTA, sodium bisulfate, ascorbic acid, ascorbyl palmitate, citric acid, glycine, L-cysteine hydrochloride, methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and others known to those of ordinary skill in the art. The amount of antioxidant or stabilizing agent may range from about 0.01 mg/mL to about 50 mg/mL of the composition, preferably from about 0.05 mg/mL to about 5 mg/mL, and most preferably from about 0.05 mg/mL to about 2 mg/mL.

The pharmaceutical compositions may optionally contain a buffering agent, which is used to resist change in pH upon dilution or addition of acid or alkali. Such compounds include, by way of example and without limitation, acetic acid, sodium acetate, adipic acid, benzoic acid, sodium benzoate, maleic acid, monobasic sodium phosphate, dibasic sodium phosphate, disodium hydrogen phosphate dodecahydrate, lactic acid, tartaric acid, potassium metaphosphate, potassium phosphate, monobasic sodium acetate, sodium bicarbonate, sodium tartrate and others known to those of ordinary skill in the art.

The pharmaceutical compositions may optionally contain a "tonicity modifier" that can be used to adjust the tonicity of the liquid formulation. Suitable tonicity modifiers include glycerine, lactose, mannitol, dextrose, sodium chloride, sodium sulphate, sorbitol, trehalose and others known to those of ordinary skill in the art. In one embodiment, the tonicity of the liquid formulation approximates that of the tonicity of blood or plasma. The amount of tonicity modifier may range from about 1 mg/mL to about 20 mg/mL of the composition, preferable from about 5-10 mg/m L. In certain embodiments, the composition may contain sodium chloride at a concentration of about 5 mg/mL to about 15 mg/mL, preferably sodium chloride at a concentration of about 5 mg/mL to about 10 mg/mL, more preferably, sodium chloride at a concentration of about 9 mg/mL. In certain embodiments, the composition will have an osmolality between about 200 to about 400 mOsm/kg, preferably between about 270 to about 340 mOsm/kg.

The present invention provides for a composition that may optionally comprise one or more preservatives. The term "preservative" refers to a substance present in a composition which can, at least in part, prevent and/or reduce decomposition of the composition. In some embodiments, the preservative may prevent and/or reduce decomposition of the composition by microbial growth in the composition.

In some embodiments, the preservative may be present in the composition at a concentration that allows for a multi-dose formulation of the composition. In some embodiments, the preservative may be present in the composition at a concentration that prevents and/or reduces decomposition of unused portions of the composition in a multi-dose formulation. In some embodiments, the preservative may allow for up to about 14 days of use, preferably up to about 30 days of use, more preferably up to about 60 days of use, and most preferably up to about 90 days of use of a multi-dose formulation of the composition. In some embodiments, the preservative may be present in the composition at a concentration of in the range of about 1 to 10 mg/mL, preferably in the range of about 3 and 7 mg/mL, more preferably in the range of about 4 and 5 mg/mL, more preferably at about 4.5 mg/mL.

Preferably, preservatives comprise one or more of benzalkonium chloride, benzethonium chloride, benzoic acid, benzyl alcohol, benzyl paraben, bronopol, butyl paraben, cetrimide, cetylpyridinium chloride, chlorobutanol, chlorhexidine, chlorocresol, chloroxylenol, cresol, ethyl alcohol, ethyl paraben, ethylparaben, glycerin, hexetidine, imidurea, isobutyl paraben, meta-cresol, methyl paraben, methylparaben, phenol, phenoxyethanol, phenylethyl alcohol, phenylmercuric nitrate, p-hydroxybenzoic acid esters, potassium sorbate, propyl paraben, propylene glycol, sodium benzoate, sodium perborate, sodium propionate, sorbic acid, stabilized thimerosal, and/or thimerosal.

The pharmaceutical compositions of the present invention may also contain pH adjusting agents or neutralizing agents. The pH adjusting agent or neutralizing agent is selected from the group consisting of sodium hydroxide, potassium hydroxide, magnesium hydroxide, methane sulfonic acid, sodium carbonate, tris, sodium linoleate, sodium oleate, potassium carbonate, potassium linoleate, potassium oleate, hydrochloric acid and mixtures thereof.

In certain non-limiting embodiments, stable dihydroergotamine compositions are formulated at a pH of between about 5.0 and about 6.0, or between about 5.2 and about 5.5. In other non-limiting embodiments, stable dihydroergotamine composition is formulated at a pH ranging from 5.0 and 6.0, preferably from 5.2 and 5.5.

In an aspect, the present invention provides a method for treating migraine in a patient in need thereof, the method comprising, providing a stable pharmaceutical composition for parenteral administration comprising i) dihydroergotamine mesylate; ii) alcohol, iii) glycerine and (iv) water for injection; and (v) optionally methane sulfonic acid and/or sodium hydroxide, wherein pH of the composition ranges from 5.0 to 6.0, preferably between 5.2 to 5.5.

In an aspect, the present invention provides a method for treating migraine in a patient in need thereof, the method comprising, providing a stable pharmaceutical composition for parenteral administration comprising i) 1 mg/mL of dihydroergotamine mesylate; ii) alcohol, iii) glycerine and (iv) water for injection; and (v) optionally methane sulfonic acid and/or sodium hydroxide, wherein pH of the composition ranges from 5.0 to 6.0, preferably between 5.2 to 5.5.

In another aspect, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) optionally methane sulfonic acid and/or sodium hydroxide, wherein pH of the composition ranges from about 5.0 to 6.0, preferably between about 5.2 to about 5.5.

In an embodiment, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) optionally methane sulfonic acid and/or sodium hydroxide, wherein pH of the composition ranges from 5.0 to 6.0, preferably between 5.2 to 5.5, and wherein the composition is stable for at least 3 months at 25° C. and 60% relative humidity.

In an embodiment, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) optionally methane sulfonic acid and/or sodium hydroxide, wherein pH of the composition ranges from 5.0 to 6.0, preferably between 5.2 to 5.5, and wherein the composition is stable for at least 3 months at 40° C. and 75% relative humidity.

In another embodiment, the present invention provides a method for treating migraine in a human in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) optionally methane sulfonic acid and/or sodium hydroxide, wherein pH of the composition ranges from 5.0 to 6.0, preferably between 5.2 to 5.5, and wherein the composition is stable for stable for at least 24 months when stored under room temperature.

In an aspect, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 to 5.5.

In another aspect, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from about 5.0 to 6.0, preferably between about 5.2 to about 5.5.

In an embodiment, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 to 5.5, and wherein the composition is stable for at least 3 months at 25° C. and 60% relative humidity.

In an embodiment, the present invention provides a method for treating migraine in a patient in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 to 5.5, and wherein the composition is stable for at least 3 months at 40° C. and 75% relative humidity.

In another embodiment, the present invention provides a method for treating migraine in a human in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 to 5.5, and wherein the composition is stable for stable for at least 24 months when stored under room temperature.

In another embodiment, the present invention provides a method for treating migraine in a human in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 to 5.5, and wherein the composition has a level of impurity D that is less than 2% as measured by HPLC, preferably less than 1% as measured by HPLC, and most preferably less than 0.5% as measured by HPLC.

In yet another embodiment, the present invention provides a method for treating migraine in a human in need thereof, the method comprising, providing a stable pharmaceutical composition for parenteral administration comprising i) 1.0 mg/mL of dihydroergotamine mesylate; ii) alcohol, iii) glycerine and (iv) water for injection; and (v) methane sulfonic acid and/or sodium hydroxide, wherein pH of the composition ranges from 5.0 to 6.0, preferably between 5.2 and 5.5, and wherein the sum of all impurities in the composition prepared according to the invention is less than 3% as measured by HPLC, preferably less than 2.5% as measured by HPLC, and most preferably less than 2% as measured by HPLC at the end of shelf-life.

In any of the above embodiments, the present application relates to stable pharmaceutical compositions of dihydroergotamine for parenteral administration, wherein said composition comprises dihydroergotamine mesylate at a concentration selected from the group of about 0.1 mg/ml or about 0.5 mg/ml or about 1 mg/ml or about 1.5 mg/1 ml or about 2 mg/ml or about. 2.5 mg/ml or about 3.0 mg/ml or about 3.5 mg/ml or about 4 mg/ml.

In another aspect, the stable pharmaceutical compositions of dihydroergotamine for parenteral administration does not exhibit any precipitation upon storage such as at 2° C.-8° C., 25° C., 40° C., or 45° C. for at least 7 days, at least 10 days, at least 11 days, at least 12 days, at least 13 days, at least 20 days, at least 30 days, at least 45 days, at least 60 days or longer.

In another aspect, the stable pharmaceutical compositions of dihydroergotamine mesylate for parenteral administration can be supplied, stored, or delivered in an ampoule or vial that is, for example, about 0.5 mL, about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL in volume.

Pharmaceutical compositions of the invention can be formulated in any suitable volume. The formulation volume can be, for example, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 2.6 mL, about 2.7 mL, about 2.8 mL, about 2.9 mL, about 3 mL, about 3.1 mL, about 3.2 mL, about 3.3 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 4.6 mL, about 4.7 mL, about 4.8 mL, about 4.9 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL, about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL.

Pharmaceutical compositions of the invention can be formulated at any suitable pH. The pH can be for example about 5, about 5.05, about 5.1, about 5.15, about 5.20, about 5.25, about 5.30, about 5.35, about 5.40, about 5.45, about 5.5, about 5.55, about 5.6, about 5.65, about 5.7, about 5.75, about 5.8, about 5.85, about 5.9, about 5.95, about 6.0 pH units.

The dihydroergotamine containing compositions demonstrate long term storage stability for at least about one year, especially when stored at the room temperature. In one embodiment, the sum of all impurities (impurity A, impurity B, impurity C, impurity D, impurity E & impurity I) in the inventive compositions is less than about 3% as determined by HPLC at a wavelength of 220 nm after at least about one year at a temperature of from about 5° C. to about 25° C.

The gas used for purging the water-for-injection or the container may be any appropriate inert gas known to those in the art, the most commonly used gases being argon, helium or nitrogen or mixtures thereof. However, the most preferred inert gas is nitrogen.

The shelf life can be at any temperature, including, for example, room temperature and refrigeration (i.e., 2-8° C.). In some embodiments, a pharmaceutical composition has a shelf life of at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 25 months, at least about 26 months, at least about 27 months, at least about 28 months, at least about 29 months, or at least about 30 months.

A formulation or unit dosage form described herein can exhibit, for example, about 0.1%, about 0.2%, about 0.3%, about 0.4%, about 0.5%, about 0.6%, about 0.7%, about 0.8%, about 0.9% about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, or about 10% degradation over a specified period of time.

The formulations of the present invention may be sterilized using methods known to the skilled artisan. Non-limiting examples of sterilization techniques include filtration through aseptic filtration-filling-sealing, terminal sterilization, incorporation of sterilizing agents, irradiation, and heating.

In certain non-limiting embodiments, sterilization may be accomplished by any of the conventional methods including aseptic filtration-filling-sealing, terminal sterilization, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 122° C. for 5 to 15 minutes.

Containers suitable according to the present invention are those known in the art. They include vials, syringes, cartridges, pre-filled syringes, auto-injectors, infusion bags and bottle presentations. In some embodiments, the container may be a single-dose formulation or a multi-dose formulation. Containers may be fabricated from glass or from polymeric materials. Suitable containers should be of a size sufficient to hold one or more doses of dihydroergotamine mesylate.

The present invention provides for compositions in single-dose and/or multidose formulations. In some embodiments, the composition may be contained in ampoules or vials. In some embodiments, the vials may be made from clear glass, amber glass, or plastic. In some embodiments, the vials or ampoules may be in the range of about 0.1 to 500 mL in volume, preferably in the range of about 0.5 to 250 mL, more preferably in the range of about 1 to 100 mL, and most preferably in the range of about 10 to 50 mL.

In some embodiments, the composition may exist in a 1 mL or 10 mL vial. In some embodiments, the 1 mL vial may be a single-dose formulation. In some embodiments, the 10 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days.

The polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate etc. In addition, crystal zenith (CZ) resin containers and similar resins can be used as rigid containers and syringes.

A pre-filled syringe comprising sterile and stable dihydroergotamine mesylate solution according to the invention will be advantageous when compared to ampoules or vials. A pre-filled syringe fabricated from a polymer will not only be convenient for handling, storage and administration, but will also minimize mixing or dosing errors. The pre-filled syringe according to the invention may also include single-use auto injectors and reusable auto injectors.

The following examples are provided for illustrative purpose only and should not be considered as limiting the scope of present invention in any way.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

General HPLC Procedure

As explained in detail below, the following HPLC procedure can be used to detect and quantify impurities of dihydroergotamine as well as assay calculation. The materials and general conditions are listed below:

TABLE 1

| Chromatographic conditions | |
|---|---|
| Chromatographic | Gradient |
| Column | Inertsil ODS-3 C18 150 mm × 4.6 mm × 3 μm |
| Column Temperature | 25° C. |
| Flow rate | 1.5 mL/min |
| Detector | 220 nm (UV) |
| Injection volume | 5 μl |
| Run time | 25 min |
| Retention time | 6.5 minutes |
| Mobile Phase A | To 1000 mL of water add 3.0 grams of sodium heptane sulphonate monohydrate and adjust pH 2.0 with dilute Ortho phosphoric acid and mix well |
| Mobile Phase B | Solution A:Acetonitrile in the ratio of 20:80 v/v. |

TABLE 2

Gradient Program

| Time (minutes) | Solution A (%) | Solution B (%) |
|---|---|---|
| 0.01 | 58 | 42 |
| 15.0 | 40 | 60 |
| 20.0 | 40 | 60 |
| 35.0 | 40 | 60 |
| 36.0 | 58 | 42 |
| 40.0 | 58 | 42 |

TABLE 3

The relative retention times (RRTs) of the related substances with respect to dihydroergotamine peaks are shown.

| # | Name of Impurity | Structure | RRT* |
|---|---|---|---|
| 1 | Impurity A: Ergotamine (6aR,9R)-N-[(2R,5S,10aS,10bS)-5-benzyl-10b-hydroxy-2-methyl-3,6-dioxooctahydro-8H-oxazolo[3,2-a]pyrrolo[2,1-c]pyrazin-2-yl]-7-methyl-4,6,6a,7,8,9-hexahydroindolo[4,3-fg]quinoline-9-carboxamide | 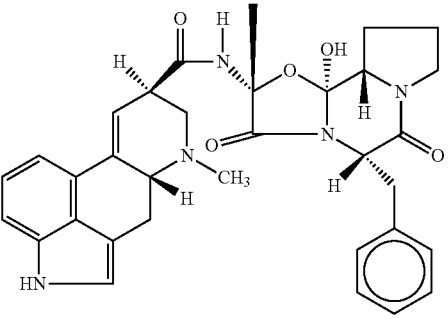 | 0.95 |

TABLE 3-continued

The relative retention times (RRTs) of the related substances with respect to dihydroergotamine peaks are shown.

| # | Name of Impurity | Structure | RRT* |
|---|---|---|---|
| 2 | Impurity B: 9,10-dihydroergostine (6aR,9R,10aR)-N-[(2R,5S,10aS,10bS)-5-benzyl-2-ethyl-10b-hydroxy-3,6-dioxooctahydro-8H-oxazolo[3,2-a]pyrrolo[2,1-c]pyrazin-2-yl]-7-methyl-4,6,6a,7,8,9,10,10a-octahydroindolo[4,3-fg]quinoline-9-carboxamide | 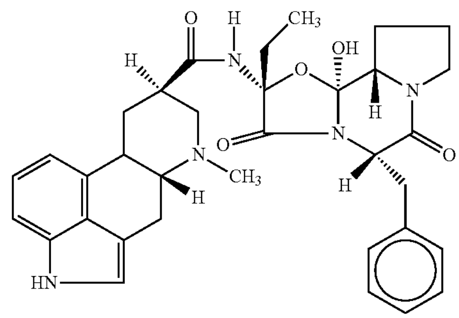 | 1.2 |
| 3 | Impurity C: 8-hydroxy-9,10-dihydroergotamine (6aR,9S,10aR)-N-[(2R,5S,10aS,10bS)-5-benzyl-10b-hydroxy-2-methyl-3,6-dioxooctahydro-8H-oxazolo[3,2-a]pyrrolo[2,1-c]pyrazin-2-yl]-9-hydroxy-7-methyl-4,6,6a,7,8,9,10,10a-octahydroindolo[4,3-fg]quinoline-9-carboxamide | 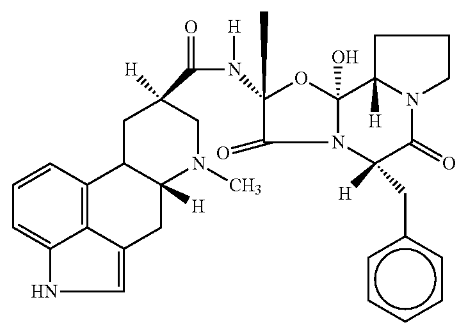 | 0.86 |
| 4 | Impurity D: 2'-epi-9,10-dihydro ergotamine (6aR,9R,10aR)-N-[(2R,5S,10aS,10bS)-5-benzyl-10b-hydroxy-2-methyl-3,6-dioxooctahydro-8H-oxazolo[3,2-a]pyrrolo[2,1-e]pyrazin-2-yl]-7-methyl-4,6,6a,7,8,9,10,10a-octahydroindolo[4,3-fg]quinoline-9-carboxamide | 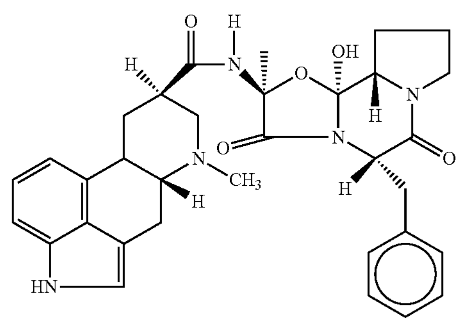 | 0.7 |
| 5 | Impurity E: Dihydroergocristine (6aR,9R,10aR)-N-[(2R,5S,10aS,10bS)-5-benzyl-10b-hydroxy-2-(1-methylethyl)-3,6-dioxo-octahydro-8H-oxazolo[3,2-a]pyrrolo[2,1-c]pyrazin-2-yl]-7-methyl-4,6,6a,7,8,9,10,10a-octahydroindolo[4,3-fg]quinoline-9-carboxamide | 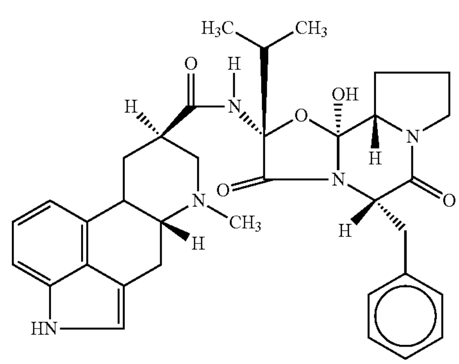 | 1.4 |

Example 1

TABLE 4

| Ingredients | Quantity | |
| --- | --- | --- |
| | mg/mL | % w/v |
| Dihydroergotamine mesylate USP | 1 | 0.1 |
| Alcohol USP | 0.061 mL | 6.1% v/v |
| Glycerine USP | 150 mg | 15 |
| Sodium hydroxide NF | q. s. to pH 5-6 | q. s. to pH 5-6 |
| Methane sulfonic acid IH | q. s. to pH 5-6 | q. s. to pH 5-6 |
| Water for Injection | q. s to 1.0 mL | q. s to 100% |

Manufacturing Process:

About 80% of the water for injection was added into the manufacturing vessel under nitrogen purging. Alcohol, followed by glycerine, was added in portions and mixed until a clear solution was formed. Dihydroergotamine mesylate was added to the clear solution, and mixing continued until there was complete dissolution. Adjust the pH with 0.05 N methane sulfonic acid or with 0.5 N sodium hydroxide to 5.0-6.0. Sufficient quantity of water was added to make up the final volume. The final solution was passed through a 0.22 μmembrane filter, and then filled into 1 mL USP Type I glass ampoule and seal the ampoules under nitrogen purging.

Comparison of individual and total impurities of dihydroergotamine mesylate injection of Example 1 in the experiments conducted at 25±2° C. and 60±5% relative humidity for 12 months using general HPLC method described above is presented in the following table.

TABLE 5

Comparative impurities data at 25 ± 2° C. and 60 ± 5% relative humidity at different pH points.

| Test parameter | Test | Reference |
| --- | --- | --- |
| pH | 5.5 | 3.7 |
| Assay | 96.5% | 94.8% |
| Impurity A | <PQL | 0.01% |
| Impurity B | 0.18% | 0.25% |
| Impurity C | <PQL | 0.09% |
| Impurity D | 0.3% | 3.9% |
| Impurity E | 0.17% | 0.08% |
| Impurity I | 0.14% | 0.14% |
| Unspecified impurity | 0.26% | 0.20% |
| Total Impurities | 1.0% | 5.5% |

The invention claimed is:

1. A method of treating migraine in a patient in need thereof, the method comprising providing a stable pharmaceutical composition comprising 1.0 mg/mL of dihydroergotamine mesylate;
   wherein the pH of the composition ranges from 5.0 to 6.0;
   wherein a level of 2'-epi-9,10-dihydro ergotamine is no greater than 2.0% w/w when stored at 25° C./60% relative humidity for 12 months as measured by HPLC, and
   wherein said pharmaceutical composition is an injectable composition.

2. The method claim 1, wherein the composition further comprises alcohol, glycerine, or a combination thereof.

3. The method of claim 2, wherein the composition further comprises a pH adjusting agent.

4. The method of claim 3, wherein the pH adjusting agent is methane sulfonic acid, sodium hydroxide or a combination thereof.

5. The method of claim 1, wherein the pH of the injectable composition ranges from 5.2 to 5.5.

6. The method of claim 1, wherein the composition comprises no greater than 2% of total impurities, as determined by HPLC.

7. The method of claim 1, wherein the injectable composition comprises no greater than 2% 1.5% of 2'-epi-9,10-dihydro ergotamine.

8. The method of claim 1, wherein the injectable composition comprises no greater than 1% of 2'-epi-9,10-dihydro ergotamine.

9. The method of claim 1, wherein the injectable composition comprises no greater than 0.5% of 2'-epi-9,10-dihydro ergotamine.

10. The method of claim 1, wherein said composition is stable for at least 3 months at 25±2° C. and 60±5% relative humidity.

11. The method of claim 1, wherein said composition is stable for at least 24 months when stored under room temperature.

* * * * *